(12) United States Patent
Suzuki et al.

(10) Patent No.: US 7,981,045 B2
(45) Date of Patent: Jul. 19, 2011

(54) APPARATUS, METHOD AND COMPUTER PROGRAM PRODUCT FOR DETERMINING RESPIRATORY CONDITION

(75) Inventors: Takuji Suzuki, Kanagawa (JP); Atsushi Sugahara, Kanagawa (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 1404 days.

(21) Appl. No.: 11/480,464

(22) Filed: Jul. 5, 2006

(65) Prior Publication Data

US 2007/0010722 A1 Jan. 11, 2007

(30) Foreign Application Priority Data

Jul. 6, 2005 (JP) ................. 2005-198082

(51) Int. Cl.
*A61B 5/08* (2006.01)
*A61B 7/00* (2006.01)
(52) U.S. Cl. ............................ 600/529; 600/586
(58) Field of Classification Search .......... 600/300, 600/529, 538, 586
See application file for complete search history.

(56) References Cited

U.S. PATENT DOCUMENTS

| | | | | |
|---|---|---|---|---|
| 5,989,193 | A * | 11/1999 | Sullivan | 600/534 |
| 6,190,328 | B1 * | 2/2001 | Ruton et al. | 600/532 |
| 6,261,238 | B1 * | 7/2001 | Gavriely | 600/532 |
| 6,409,676 | B2 * | 6/2002 | Ruton et al. | 600/532 |
| 6,569,094 | B2 | 5/2003 | Suzuki et al. | |
| 6,607,484 | B2 | 8/2003 | Suzuki et al. | |
| 6,942,615 | B2 | 9/2005 | Suzuki et al. | |
| 6,985,078 | B2 | 1/2006 | Suzuki et al. | |
| 2004/0127807 | A1 * | 7/2004 | Hatlesad et al. | 600/529 |

FOREIGN PATENT DOCUMENTS

| | | |
|---|---|---|
| JP | 4-82538 | 3/1992 |
| JP | 8-131421 | 5/1996 |
| JP | 2001-70256 | 3/2001 |
| JP | 2004-33254 | 2/2004 |
| JP | 2004223026 A * | 8/2004 |
| JP | 2004-357758 | 12/2004 |

OTHER PUBLICATIONS

Hiroshi Nakano, et al., "Detection of Respiratory Effort During Sleep Apnea by Tracheal Sounds Analysis", Clinical Pharmacology and Therapy, 9, 4, Jul. 1999, pp. 387-393 (with English abstract).

Hirotaka Hara, "Snoring and Sleep Apnea Syndrome: Clinical Significance of Acoustic Analysis of Snoring Sound", Department of Otolaryngology and Specific Organ Medicine, Yamaguchi University School of Medicine, 53, 6, Dec. 2004, pp. 265-267 (with partial English translation).

U.S. Appl. No. 11/512,241, filed Aug. 30, 2006, Ouchi et al.

* cited by examiner

*Primary Examiner* — Patricia C Mallari
*Assistant Examiner* — Christian Jang
(74) *Attorney, Agent, or Firm* — Oblon, Spivak, McClelland, Maier & Neustadt, L.L.P.

(57) ABSTRACT

An apparatus for determining a respiratory condition includes a breath sound measuring unit 111 measuring a breath sound passing through a subject's airway by a breathing; a frequency converting unit 132 converting a frequency on the breath sound to obtain a frequency spectrum; a respiratory synchronous component extracting unit 134 extracting a respiratory synchronous component, which varies depending on the breathing, from the frequency spectrum; a frequency distribution detecting unit 136 detecting a frequency distribution of the respiratory synchronous component; and a respiratory condition determining unit 138 determining a subject's respiratory condition based on the frequency distribution. According to the apparatus, various symptoms, such as airway occlusion, respiratory obstruction and the like in relation to breathing during sleep can be determined.

15 Claims, 7 Drawing Sheets

APPARATUS, METHOD AND COMPUTER PROGRAM PRODUCT FOR DETERMINING RESPIRATORY CONDITION

CROSS-REFERENCE TO RELATED APPLICATIONS

This application is based upon and claims the benefit of priority from the prior Japanese Patent Application No. 2005-198082, filed on Jul. 6, 2005; the entire contents of which are incorporated herein by reference.

BACKGROUND OF THE INVENTION

1. Field of the Invention

The present invention relates to an apparatus, a method and a computer program product for determining a respiratory condition that determines a subject's respiratory condition.

2. Description of the Related Art

In recent years, drivers' falling asleep while driving a moving vehicle, such as a rail, a car or the like, has resulted in road accidents. A sleep apnea syndrome has recently received attention as one of the causes of the road accidents. Further, people may experience hypoxic condition, but not apnea, which may result from improper pillow height.

In addition, a chair-type child seat or a stroller causes hypoxia to children. Further, there is an increasing incidence of chronic obstructive pulmonary disease (COPD), in which an asthma attack is likely to occur during sleep, which affects, for example, 16 million people in America. Therefore, measurement of a respiratory condition during sleep has received attention.

In order to measure a respiratory condition during sleep, the degree of restrictions needs to be low. Therefore, a method for measuring heart and respiratory rates by providing a sensor in a pillow or a mattress has been researched and developed. A method for measuring respiratory-related sounds such as snoring by an external microphone has also been devised. Further, a method for measuring a pulmonary sound and a sound called rales, which is generated during asthma, by a sound sensor provided on a body has been examined (JP-A 2004-357758 (KOKAI)).

As described above, the heart rate respiratory sensor embedded in a bed measures low-frequency vibration (up to 1 Hz) according to movements of the chest based on a breathing. Therefore, it is difficult to make measurement when airway occlusion, bruxism, or the like occurs, which has a high frequency range, even though complete apnea does not occur. In addition, it is not possible for the external microphone to make measurement, when snoring, bruxism or the like does not appear to the outside as sounds. Therefore, it is difficult to detect a change in breath sounds due to the state of respiratory obstruction.

SUMMARY OF THE INVENTION

According to one aspect of the present invention, an apparatus for determining a respiratory condition includes a breath sound measuring unit measuring a breath sound passing through a subject's airway; a frequency converting unit converting a frequency on the breath sound to obtain a frequency spectrum; a respiratory synchronous component extracting unit extracting a respiratory synchronous component, which varies depending on the breathing, from the frequency spectrum; a frequency distribution detecting unit detecting a frequency distribution of the respiratory synchronous component; and a respiratory condition determining unit determining a subject's respiratory condition based on the frequency distribution.

According to another aspect of the present invention, a method of determining respiratory condition includes measuring a breath sound passing through a subject's airway; converting a frequency on the breath sound to obtain a frequency spectrum; extracting a respiratory synchronous component, which varies depending on the breathing, from the frequency spectrum; detecting a frequency distribution of the respiratory synchronous component; and determining a subject's respiratory condition based on the frequency distribution.

A computer program product according to still another aspect of the present invention causes a computer to perform the method according to the present invention.

BRIEF DESCRIPTION OF THE DRAWINGS

FIG. 4 is a diagram illustrating a detailed configuration of a sensor array and the like;

DETAILED DESCRIPTION OF THE INVENTION

Hereinafter, preferred embodiments of an apparatus, a method and a computer program product for determining a respiratory condition according to the present invention will be described in detail with reference to the accompanying drawings.

First Embodiment

Figure 1:
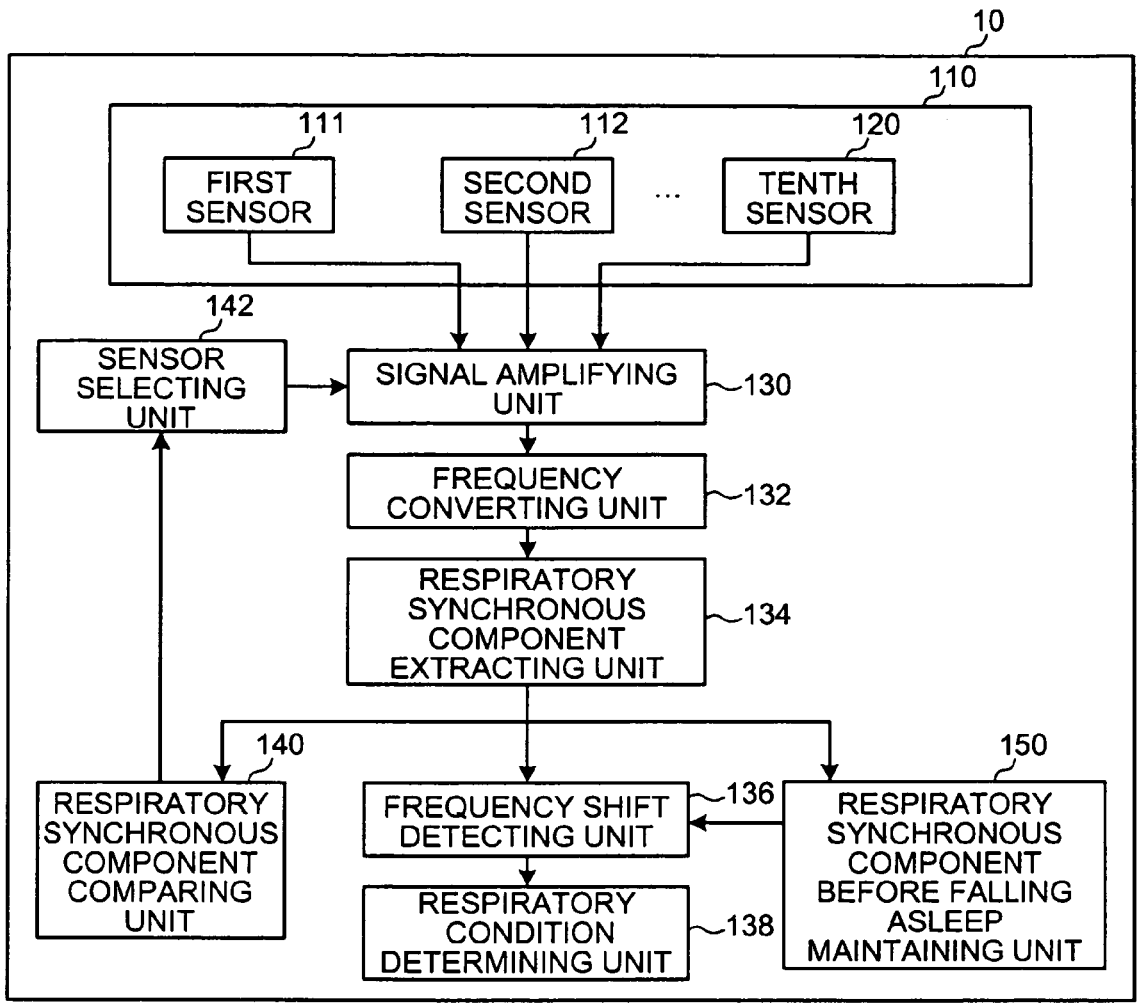
FIG. 1 is a block diagram illustrating an entire configuration of an apparatus for determining a respiratory condition according to a first embodiment of the present invention.

FIG. 1 is a block diagram illustrating an entire configuration of an apparatus for determining a respiratory condition 10 according to a first embodiment of the present invention. The apparatus for determining a respiratory condition 10 includes a sensor array 110 having a plurality of sensors 111 to 120 that detect breath sounds passing through a subject's airway while being in contact with the subject's skin, a signal amplifying unit 130, a frequency converting unit 132, a respiratory synchronous component extracting unit 134, a frequency shift detecting unit 136, a respiratory condition determining unit 138, a respiratory synchronous component comparing unit 140, a sensor selecting unit 142, and a respiratory synchronous component, before falling asleep, maintaining unit 150.

The signal amplifying unit 130 amplifies breath sound signals detected from the respective sensors 111 to 120. The frequency converting unit 132 performs frequency conversion, such as Fourier transform, so as to obtain frequency spectrums from the amplified breath sound signals.

The respiratory synchronous component extracting unit 134 extracts a respiratory synchronous component from the frequency spectrum obtained by the frequency converting unit 132. Here, the respiratory synchronous component refers to a component which is changed in synchronous with the subject's breathing and is present within the frequency spectrum obtained by the frequency converting unit 132.

The respiratory synchronous component, before falling asleep, maintaining unit 150 maintains a subject's respiratory synchronous component before falling asleep. Specifically, a respiratory synchronous component is obtained from the subject's breath sound before falling asleep according to processes from the signal amplifying unit 130 to the respiratory synchronous component extracting unit 134. The obtained respiratory synchronous component is maintained as a respiratory synchronous component before falling asleep. A respiratory condition before falling asleep may be considered as a normal state. Therefore, the respiratory synchronous component obtained at this time is maintained as the respiratory synchronous component in the normal state (healthy state).

The frequency shift detecting unit 136 detects a frequency component change, namely a frequency shift in the respiratory synchronous component obtained by the respiratory synchronous component extracting unit 134. The respiratory condition determining unit 138 determines a respiratory condition based on the frequency shift detected by the frequency shift detecting unit 136.

The respiratory synchronous component comparing unit 140 compares each of the respiratory synchronous components detected by the respiratory synchronous extracting unit 134 to each of the breath sound signals detected by the respective sensors 111 to 120. The sensor selecting unit 142 selects one sensor among the plurality of sensors 111 to 120 based on the comparison result from the respiratory synchronous component comparing unit 140. Here, the selected sensor detects a breath sound that becomes a target for the respiratory condition determining unit 138 to determine a respiratory condition.

Figure 2:
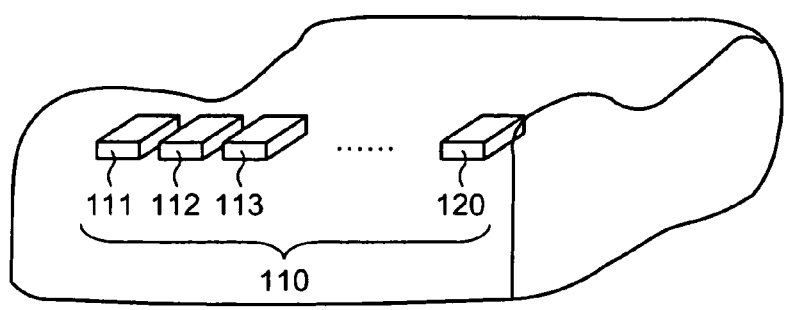
FIG. 2 is a diagram illustrating the external appearance of a pillow including the apparatus for determining a respiratory condition.

FIG. 2 is a diagram illustrating the external appearance of a pillow including the apparatus for determining a respiratory condition 10. As shown in FIG. 2, a portion of the pillow, with which a subject's neck comes in contact, has a more convex shape than any other portions thereof. The plurality of sensors 111 to 120 are arranged in a row in the convex portion along a horizontal direction of the pillow.

Due to the subject turning over during sleep, the subject may not have contact with a predetermined sensor. However, since a plurality of sensors are provided, any one of the sensors will always be in contact with the subject, thereby enabling to detect a breath sound signal.

Figure 3:
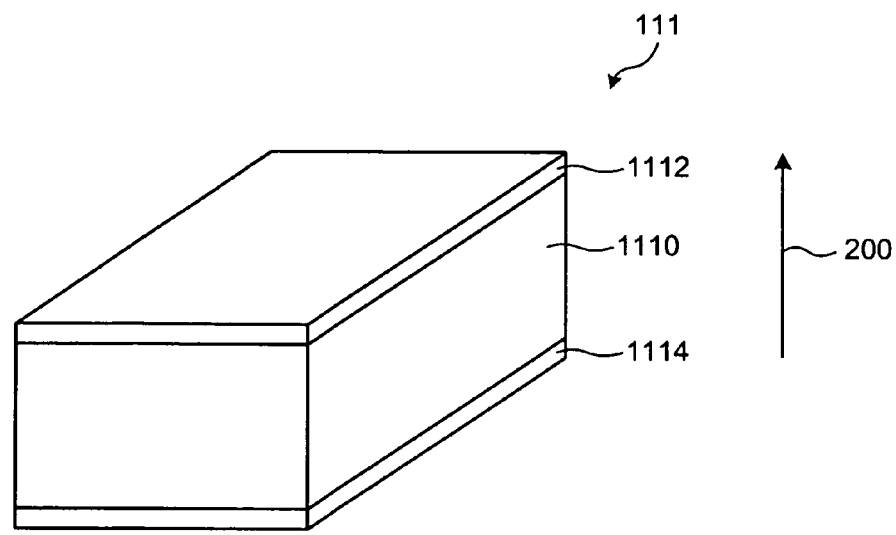
FIG. 3 is a diagram illustrating the external appearance of a first sensor.

FIG. 3 is a diagram illustrating the external appearance of the first sensor 111. The first sensor 111 includes a substrate 1110 formed of a dielectric material, such as polyimide, polyester, or the like, and electrodes 1112 and 1114 disposed at both ends of the substrate 1110. The sensor 111 is about 2 mm in thickness in a direction 200 of the electrodes 1112 and 1114. In addition, the electrodes 1112 and 1114 are 3 cm×3 cm in size. The other sensors 112 to 130 have the same configuration as the first sensor 111. In view of detecting of a change in breathing, which is generated when the throat closes, it is preferable that the respective sensors be capable of detecting a frequency of several hundreds of Hz in all cases.

In addition, the respective sensors 111 to 120 according to the present embodiment are separately formed, but, instead, it is possible to integrally form the sensors 111 to 120.

Figure 4:
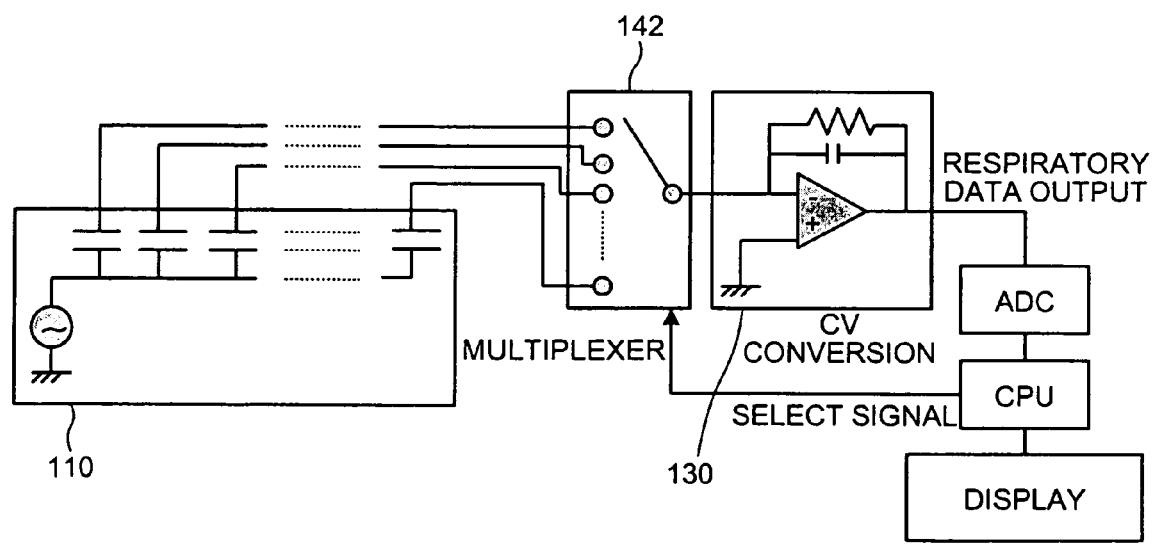

FIG. 4 is a diagram illustrating a detailed configuration of the sensor array 110 and the like. Capacitor microphones are used as the sensors 111 to 120, and a direct current bias voltage is applied thereto. A multiplexer is used in a sensor selecting unit 142. In addition, a CV converting circuit is used in the signal amplifying unit 130, and the amplification is performed after the voltage conversion. The amplified signal is AD converted and input to a CPU. In the CPU, the frequency converting unit 132, the respiratory synchronous component extracting unit 134, the frequency shift detecting unit 136, the respiratory condition determining unit 138, the respiratory synchronous component comparing unit 140, the sensor selecting unit 142, and the respiratory synchronous component, before falling asleep, maintaining unit 150 perform their processes.

The CPU selects a sensor based on the respiratory synchronous component obtained by the respective sensors, and inputs a select signal, which specifies the selected sensor, to the multiplexer. The multiplexer selects the predetermined sensor according to the select signal.

Meanwhile, a pressure sensor may be used as the sensor instead of the capacitor microphone. In this case, a sine wave of an alternating current of about 100 kHz is applied. After the signal amplification, the amplified signal is detected at a frequency equivalent to the applied voltage so as to remove an applied frequency component. Then, the signal is AD converted. As another example, after the signal amplification, the applied frequency component may be removed by a low-pass filter.

Figure 5:
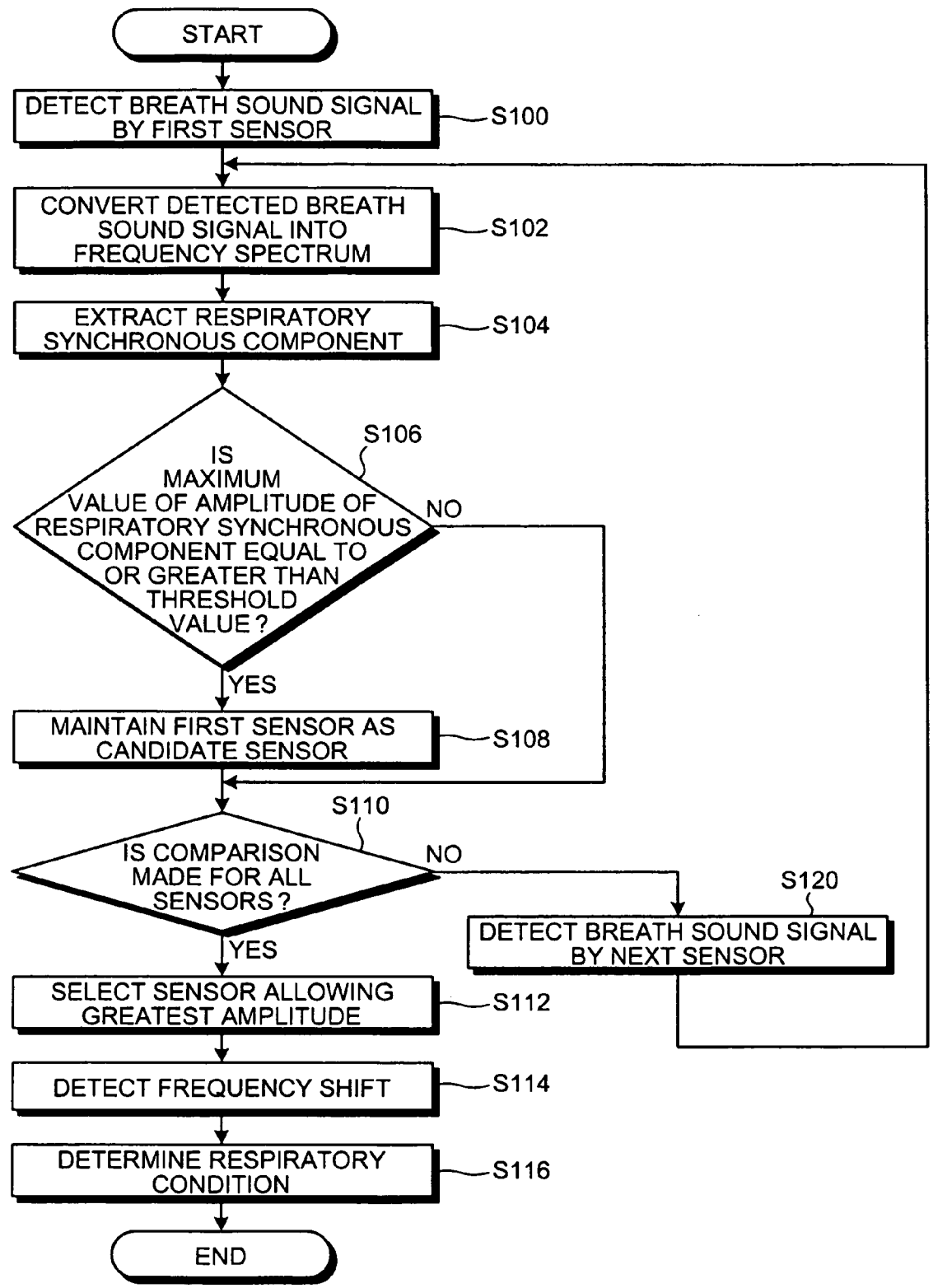
FIG. 5 is a flowchart illustrating a respiratory condition determining process in the apparatus for determining a respiratory condition.

FIG. 5 is a flowchart illustrating a respiratory condition determining process in the apparatus for determining a respiratory condition 10. First, a respiratory synchronous component is extracted with respect to a breath sound signal of the subject who is sleeping, which is detected by a predetermined sensor, for example, the first sensor 111.

Specifically, first, the first sensor 111 detects a breath sound signal of the subject who is sleeping (step S100). Next, the breath sound signal obtained by the first sensor 111 is amplified, and then frequency-converted by the frequency converting unit 132, thereby obtaining a frequency spectrum (step S102).

The respiratory synchronous component extracting unit 134 extracts a respiratory synchronous component from the frequency spectrum (step S104). Here, the respiratory synchronous component detected at this time is referred to as a respiratory synchronous component during sleep.

Figure 6:
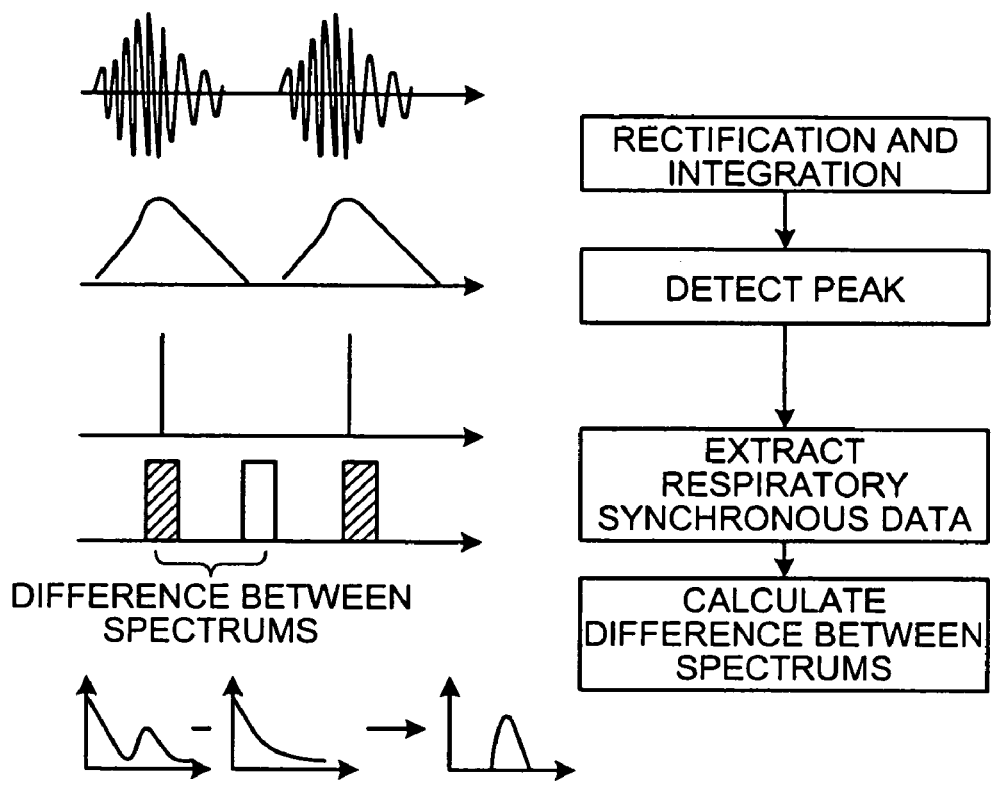
FIG. 6 is a diagram illustrating a process for extracting a respiratory synchronous component (step S104 in FIG. 5)

FIG. 6 is a diagram illustrating the process for extracting a respiratory synchronous component (step S104). As shown in FIG. 6, first, an output of the sensor is subjected to rectifying integration so as to obtain an envelope curve. Then, the maximum value and the minimum value on the envelope curve are detected. Based on time data of each of the detected maximum value and minimum value, frequency conversion is performed, and a frequency spectrum of each of the maximum value and the minimum value is obtained. The difference between the frequency spectrums is extracted as a respiratory synchronous component.

Again, the description will be made with reference to FIG. 5. After the respiratory synchronous component is extracted (step S104), the maximum value of the amplitude of a time waveform of the extracted respiratory synchronous component is compared with a predetermined threshold value. When the maximum value of the amplitude is equal to or greater than the threshold value (step S106, Yes), it is determined that the sensor can reliably detect a breath sound. Therefore, the corresponding sensor is maintained as the candidate sensor (step S108).

In contrast, when the maximum value of the amplitude is less than the threshold value (step S106, No), it is determined that the detection result is not appropriate. Therefore, the sensor is not maintained as the candidate sensor, and the process proceeds to step S110.

With respect to all of the sensors 111 to 120, when the comparison between the maximum value of the amplitude of the respiratory synchronous component and the threshold value are not completed (step S110, No), a breath sound signal is detected in another sensor for which the comparison is not completed (step S120). Then, the process returns to step S102, a frequency spectrum is obtained from the detected breath sound signal.

When the comparisons for all of the sensors are completed (step S110, Yes), the sensor, which has detected the respiratory synchronous component having the greatest amplitude of the time waveform, is selected among the candidate sensors maintained in step S108 (step S112). Accordingly, the sensor to be utilized for the breathing determination can be selected.

Then, the frequency shift detecting unit 136 compares the respiratory synchronous component during sleep, which is obtained from the detection result of the selected sensor, with the respiratory synchronous component before falling asleep, which is maintained by the respiratory synchronous component, before falling asleep, maintaining unit 150. Further, the frequency shift detecting unit 136 detects a frequency shift of the respiratory synchronous component during sleep detected by the selected sensor with respect to the respiratory synchronous component before falling asleep (step S114). Then, the respiratory condition determining unit 138 determines a respiratory condition based on the detected frequency shift (step S116).

Specifically, the respiratory condition determining unit 138 determines that respiratory is in an obstructive state when a frequency, at which the respiratory synchronous component of the selected sensor is the greatest, is shifted exceeding a predetermined value previously set based on respiratory synchronous component before falling asleep.

In addition, a respiratory synchronous component before falling asleep is detected and maintained before the subject falls asleep. Specifically, before the subject falls asleep, the respiratory synchronous component of the sensor selected through the processes of steps S100 to S112 is detected as the respiratory synchronous component before falling asleep.

Furthermore, in the present embodiment, a frequency at which the respiratory synchronous component is the greatest is used as a reference. However, a frequency at which the respiratory synchronous component becomes an intermediate value, that is, a center frequency is used as a reference instead of a frequency at which the respiratory synchronous component is the greatest. As another example, a centroid frequency is also used as a reference.

Figure 7A:
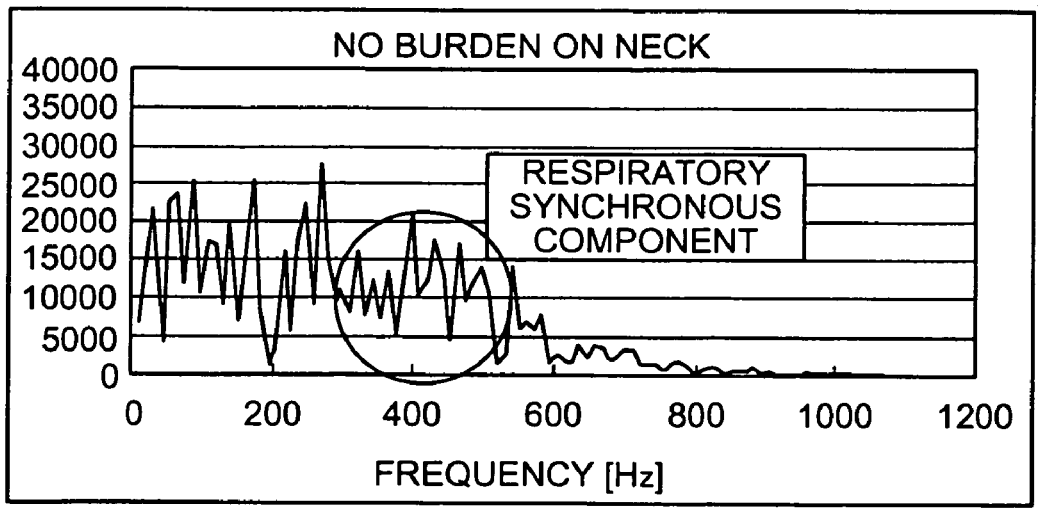
FIG. 7A is a diagram illustrating a respiratory synchronous component in a normal state.
Figure 7B:
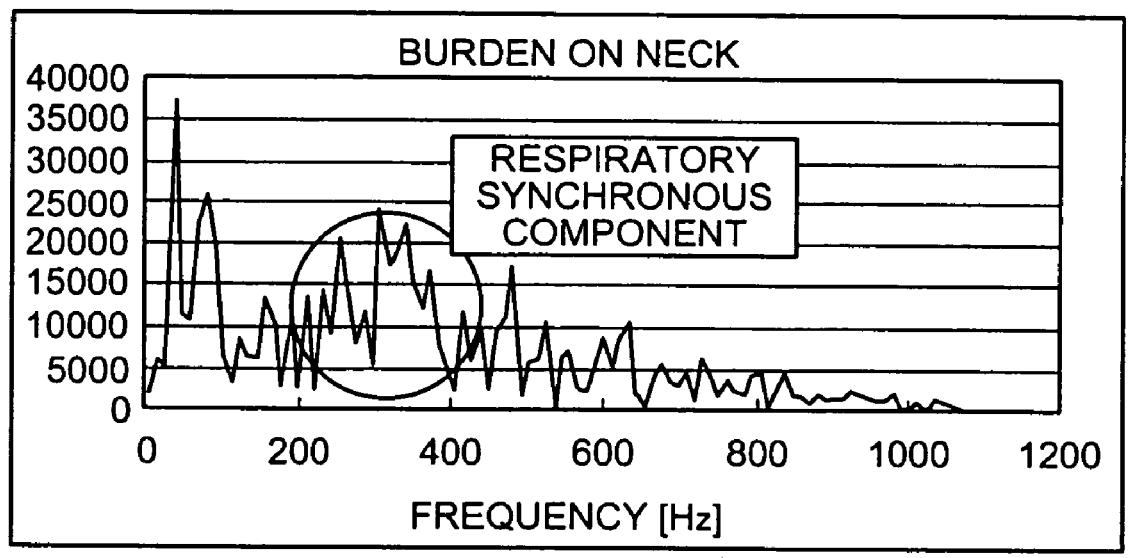
FIG. 7B is a diagram illustrating a respiratory synchronous component when a respiratory condition becomes worse.

FIGS. 7A and 7B are diagrams illustrating a frequency shift of a respiratory synchronous component. FIG. 7A is a diagram illustrating a respiratory synchronous component in a normal state. FIG. 7B is a diagram illustrating a respiratory synchronous component when a respiratory condition becomes worse. A peak of the respiratory synchronous component in the normal state, which appears around 400 Hz, shifts toward a lower frequency as shown in FIG. 7B, when a pillow is too high for example, imposing a burden on the subject's neck. That is, by detecting the frequency shift, an abnormal state, such as a case where the throat closes due to burden in the subject's neck, can be detected.

In addition, data shown in FIGS. 7A and 7B are frequency spectrums obtained by frequency conversion of all the measured sounds which are measured by the sensors. In actual, the respiratory synchronous component is extracted based on the difference between the obtained frequency spectrum and a frequency spectrum in which a breath sound is not included.

The determination result of a respiratory condition, obtained by the above-mentioned respiratory condition determining process, may be shown, for example, on a graph. Specifically, the number of times the respiratory condition becomes worse overnight, accumulated time, and the like may be displayed on a monitor when the subject wakes up. For another example, the number of times the respiratory condition becomes worse over time may be shown on a graph.

Figure 8:
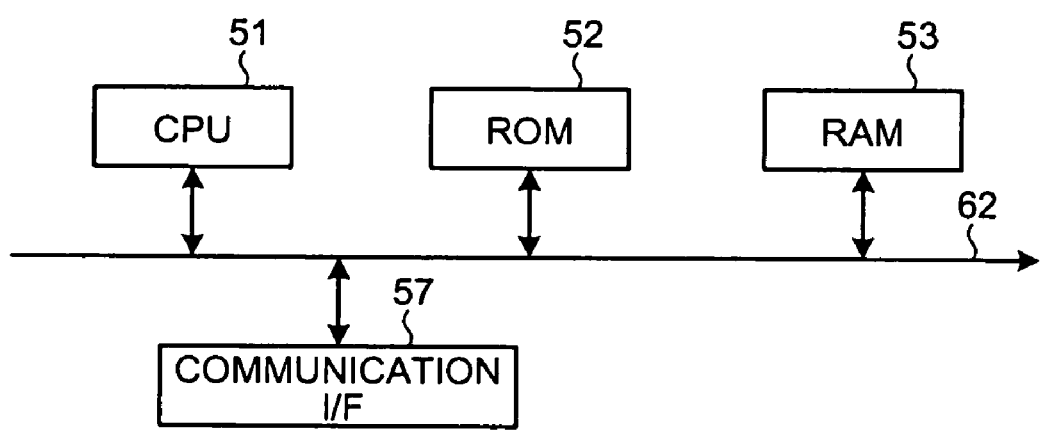
FIG. 8 is a diagram illustrating a hardware configuration of the apparatus for determining a respiratory condition according to the first embodiment.

FIG. 8 is a diagram illustrating a hardware configuration of the apparatus for determining a respiratory condition 10 according to the first embodiment. The apparatus for determining a respiratory condition 10 includes, as the hardware configuration, a ROM 52 that stores a respiratory condition determining program, which executes a respiratory condition determining process, or the like, in the apparatus for determining a respiratory condition 10, a CPU 51 that controls parts of the apparatus for determining a respiratory condition 10 according to the program in the ROM 52, a RAM 53 that stores various data for the control of the apparatus for determining a respiratory condition 10, a communication I/F 57 that is connected to a network and performs communication, and a bus 62 that connects each of the parts.

The respiratory condition determining program in the apparatus for determining a respiratory condition 10 may be provided in a state where it is recorded on a recording medium with a file installable or executable format, which can be read by a computer, such as a CD-ROM, a floppy disc (FD), a DVD or the like.

In this case, the respiratory condition determining program is read and executed from the recording medium in the apparatus for determining a respiratory condition 10, and thus, the program is loaded to a main memory unit and the parts explained above in the software construction are generated on the main memory unit.

In addition, the respiratory condition determining program of the present embodiment may be stored in a computer connected to the network, such as the Internet, such that it may be downloaded through the network.

Although the present invention has been described with the embodiment of the present invention, it will be apparent to those skilled in the art that various modifications and changes may be made.

In the embodiment, in step S106, the maximum value of the amplitude of the time waveform of the respiratory synchronous component is compared with the threshold value. Instead, in a first modification, the maximum value of a correlation function of the respiratory synchronous component is compared with a predetermined threshold value with respect to the correlation. When the maximum value of the correlation function of the respiratory synchronous component is equal to or greater than the threshold value, the sensor may be maintained as a candidate sensor (step S108). Even in this case, it is also possible to select the corresponding sensor as a candidate sensor, that is, the corresponding sensor that reliably detects a breath sound.

Further, the apparatus for determining a respiratory condition 10 according to the present embodiment determines a subject's respiratory condition according to a frequency shift based on the subject's respiratory synchronous component before falling asleep. In a second modification, however, the apparatus for determining a respiratory condition 10 may determine a subject's sleeping state according to a frequency shift based on a respiratory synchronous component previously obtained from the subject's breath sound.

Specifically, the respiratory synchronous component, obtained when the apparatus for determining a respiratory condition 10 determines a state of health while the subject is sleeping, is maintained as subject's history information. Also, it is possible to detect a frequency shift based on the respiratory synchronous component maintained as the history information.

In addition, when a plurality of respiratory synchronous components are maintained as history information, an average value or the standard deviation of the plurality of respiratory synchronous components may be calculated, and a frequency shift may be detected based on the calculated respiratory synchronous component.

In addition, in a third modification, the time when a breath sound occurs may be further detected based on the detection result from the sensor. By obtaining the breath sound at this time, it is possible to omit the process of rectification and integration, and the like, described in the embodiment.

Furthermore, in the present embodiment, a sensor to be used for determination of a sleeping state is selected based on the maximum value of the amplitude. However, in a fourth modification, it is possible to select a sensor based on an electric change in impedance between neighboring sensors, in addition to the maximum value of the amplitude.

Specifically, based on the measurement result of electric changes in impedance between neighboring sensors, a sensor in contact with the subject is selected as a first candidate sensor. In addition, with respect to the first candidate sensor selected based on the changes in impedance, as described in the embodiment, a second candidate sensor is selected by comparing the maximum value of the amplitude and the threshold value. Further, a sensor of which the detected result shows the greatest amplitude is selected among the second candidate sensors.

As a result, it is possible to expedite the process for selecting sensors by performing the sensor selection in two steps. Also, here, the first candidate sensor corresponds to the candidate sensor in the appended claims.

In addition, in a fifth modification, the apparatus for determining a respiratory condition 10 may be embedded in a bed, and may be embedded in a sheet instead of a pillow.

Second Embodiment

Figure 9:
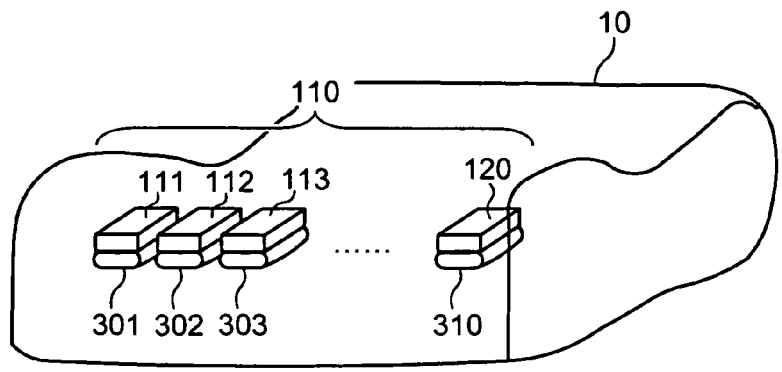
FIG. 9 is a diagram illustrating the external appearance of an apparatus for determining a respiratory condition according to a second embodiment.

FIG. 9 is a diagram illustrating the external appearance of an apparatus for determining a respiratory condition 10 according to a second embodiment. A plurality of air bags 301 to 310 are provided under respective sensors 111 to 120. In this case, one air bag is provided so as to correspond to one sensor. The air bag according to the present embodiment corresponds to a pressing member described in the appended claims.

Figure 10:
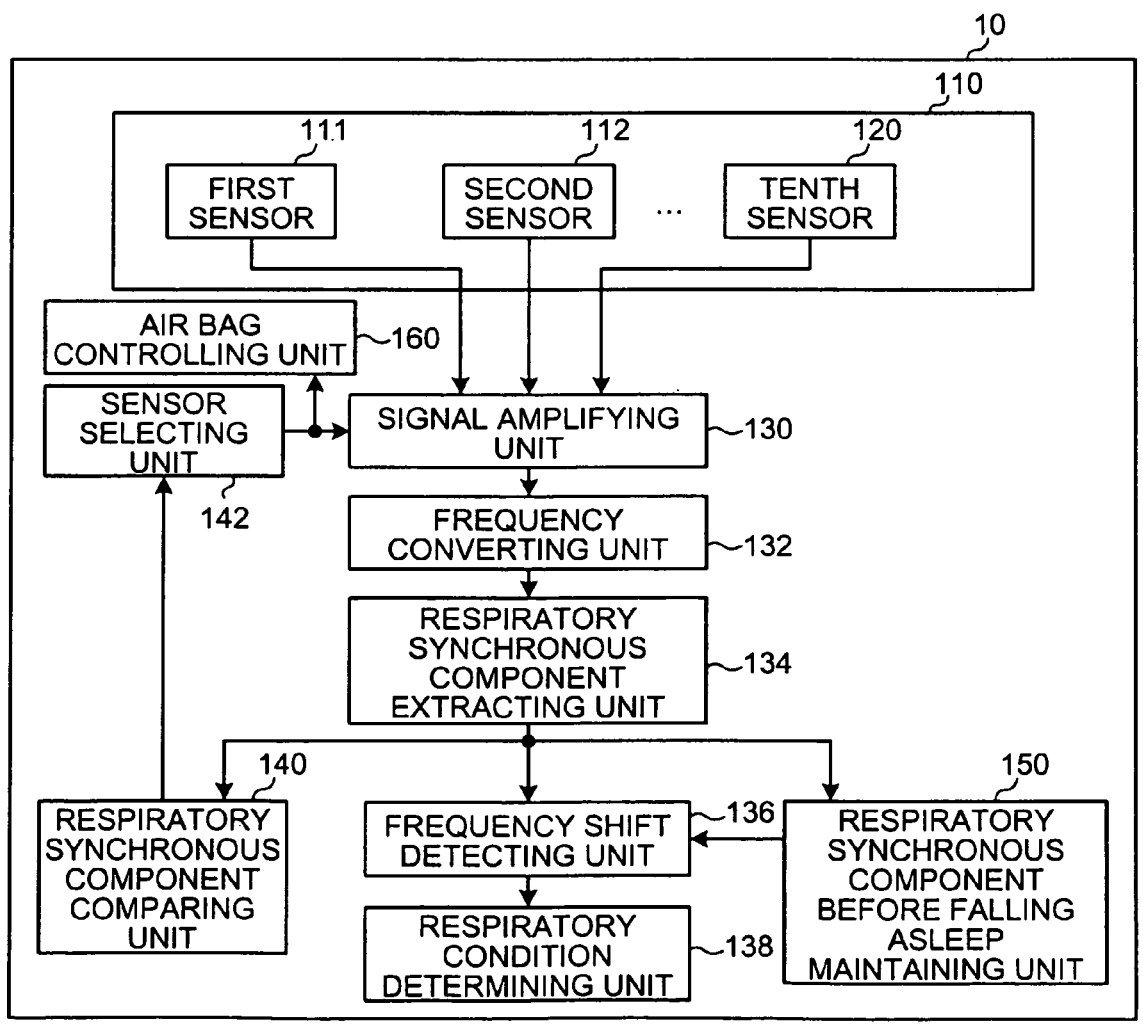
FIG. 10 is a block diagram illustrating a functional configuration of an apparatus for determining a respiratory condition according to the second embodiment.

FIG. 10 is a block diagram illustrating a functional configuration of the apparatus for determining a respiratory condition 10 according to the second embodiment. The apparatus for determining a respiratory condition 10 according to the second embodiment further includes an air bag controlling unit 160, in addition to the functional configuration of the apparatus for determining a respiratory condition 10 according to the first embodiment. The air bag controlling unit 160 outputs to the air bag an instruction that the air bag, on which a sensor selected by the sensor selecting unit 142 is mounted, is expand more.

The air bag, on which the sensor selected for the breathing determination is mounted, is expanded, thereby increasing pressure being applied to the subject. Accordingly, sensitivity in the selected sensor can be improved.

For example, in the apparatus for determining a respiratory condition 10 shown in FIG. 9, it is assumed that the first sensor 111 is selected. In this case, the first air bag 301 having the first sensor 111 mounted thereon is expanded.

Except for the above, the apparatus for determining a respiratory condition 10 according to the second embodiment has the same configuration and process as the apparatus for determining a respiratory condition 10 according to the first embodiment.

In a first modification of the apparatus for determining a respiratory condition 10 according to the second embodiment, a plurality of sensors may be provided, and the respective sensors may not be provided so as to correspond to the respective air bags. For example, two sensors may be mounted on one air bag.

In addition, in a second modification, heart rates and respiratory signals may be measured by measuring vibration transmitted to the air bag by using a pressure sensor. The total sleeping state may be further managed by a combination of the heart rate, and breathing determination and measurement results.

For example, based on the heart rates and respiratory signals obtained from the air bag, a state of an autonomic nerve, a sleep depth, a respiratory condition (apnea and snoring) and the like are measured. In addition, bruxing or a change in breathing is measured by the sensor. Then, the overall results are shown on a display.

In a third modification, based on the respiratory signal obtained by measuring the vibration, transmitted to the air bag, by using the pressure sensor, timing of a respiratory peak can be detected and utilized to detect the respiratory synchronous component in FIG. 6.

In addition, in a forth modification, the air bag controlling unit 160 may expand an air bag having another sensor mounted thereon other than the sensor selected to be utilized for sleeping state determination, that is, an air bag having a low-sensitivity sensor thereon. Accordingly, sensor sensitivity can be improved.

In addition, in a fifth modification, in a view that a sensor is securely pressed against the subject, a spring may be provided instead of the air bag. A member, which is capable of securely pressing the sensor, may be used, and it is not limited to the embodiment.

Third Embodiment

Figure 11:
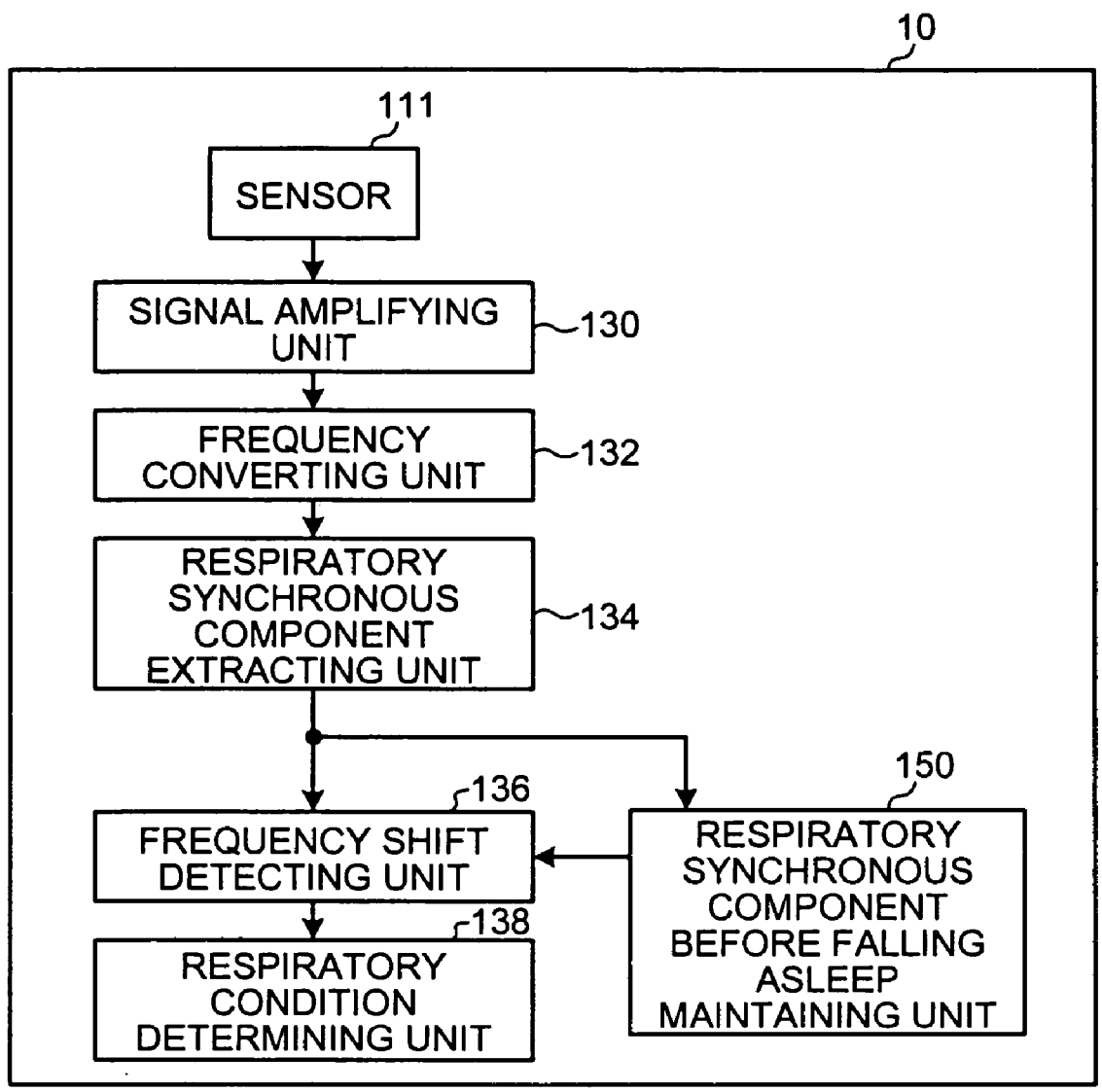
FIG. 11 is a block diagram illustrating a functional configuration of an apparatus for determining a respiratory condition according to a third embodiment.

FIG. 11 is a block diagram illustrating a functional configuration of an apparatus for determining a respiratory condition 10 according to a third embodiment. The apparatus for determining a respiratory condition 10 according to the third embodiment does not include the respiratory synchronous component comparing unit 140 and the sensor selecting unit 142. In addition, only one sensor is provided. In this configuration, the apparatus for determining a respiratory condition 10 according to the third embodiment is different from the apparatus for determining a respiratory condition 10 according to the other embodiments.

The apparatus for determining a respiratory condition 10 according to the third embodiment may be mounted in a stethoscope or the like. A doctor or a subject searches for a portion suitable for measurement while checking by the stethoscope or the like, and thus detects a breath sound signal through the stethoscope in a state where the sensor is in contact with the appropriate position.

Accordingly, the apparatus for determining a respiratory condition 10 according to the third embodiment does not perform a process for selecting an appropriate sensor, and determines a respiratory condition based on the detection result from the one sensor.

Except for the above, the apparatus for determining a respiratory condition 10 according to the third embodiment has the same configuration and process as the apparatus for determining a respiratory condition 10 according to the first embodiment. Therefore, the description thereof is not repeated.

As mentioned above, according to the present invention, various symptoms, such as airway occlusion, respiratory obstruction and the like in relation to breathing during sleep can be determined.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An apparatus for determining a respiratory condition comprising:
    a breath sound measuring unit measuring a breath sound signal passing through a subject's airway by a breathing;
    a respiratory synchronous component extracting unit calculating a first frequency spectrum and a second frequency spectrum by performing frequency conversion, the first frequency spectrum being a frequency spectrum of the breath sound corresponding to a maximum value on an envelope curve, the second frequency spectrum being a frequency spectrum of the breath sound corresponding to a minimum value on the envelope curve, the envelope curve being obtained by performing rectifying integration of the breath sound signal and extracting a respiratory synchronous component that is difference between the first frequency spectrum and the second frequency spectrum; and
    a respiratory condition determining unit determining a subject's respiratory condition worsens when a frequency shift is equal to or greater than a predetermined value, the frequency shift indicating a change between a respiratory synchronous component when the subject is in a normal state and the extracted respiratory synchronous component.

2. The apparatus according to claim 1, wherein the respiratory condition determining unit determines that the respiratory condition worsens when a frequency shift toward a lower frequency is equal to or greater than the predetermined value.

3. The apparatus according to claim 1, wherein the respiratory condition determining unit determines that the respiratory condition worsens when the frequency shift in a predetermined frequency band of the respiratory synchronous component during sleep is equal to or greater than a predetermined value.

4. The apparatus according to claim 2, further comprising:
    a normal frequency distribution maintaining unit maintaining, as a respiratory synchronous component when the subject is in a normal state, a respiratory synchronous component before the subject falls asleep; wherein
    the respiratory condition determining unit determines that the respiratory condition worsens when a frequency shift indicating a change between the respiratory synchronous component maintained in the normal frequency distribution maintaining unit and the extracted respiratory synchronous component is equal to or greater than a predetermined value.

5. The apparatus according to claim 4, wherein the breath sound measuring unit measures a breath sound before falling asleep in the condition before the subject falls asleep, and the normal frequency distribution maintaining unit maintains the respiratory synchronous component, which is extracted by the respiratory synchronous component extracting unit, based on the breath sound before falling asleep.

6. The apparatus according to claim 1, wherein the breath sound measuring unit is embedded in a bed.

7. The apparatus according to claim 6, wherein the breath sound measuring unit is embedded in a pillow.

8. The apparatus according to claim 1 further comprising:
    a plurality of the breath sound measuring units measuring breath sound passing through the subject's airway, in a state where the plurality of breath sound measuring units are in contact with the subject's skin at different positions; and
    a selecting unit of the breath sound measuring unit selecting the breath sound measuring unit utilized for the determination of a respiratory condition among the plurality of breath sound measuring units based on the plurality of respiratory synchronous components obtained from the breath sound measured by the plurality of the breath sound measuring units,
    wherein the respiratory condition determining unit determines the respiratory condition based on the breath sound measured by the breath sound measuring unit selected by the selecting unit of the breath sound measuring unit.

9. The apparatus according to claim 8, wherein the selecting unit of the breath sound measuring unit selects the breath sound measuring unit which exhibits greatest amplitude of the respiratory synchronous component.

10. The apparatus according to claim 8 further comprising:
    an impedance change detecting unit detecting changes in impedance between neighboring two electrodes, wherein the respective breath sound measuring units are disposed adjacent to each other, and
    the selecting unit of the breath sound measuring unit selects the breath sound measuring unit utilized for the determination of a respiratory condition based on the changes in impedance between the electrodes, which are detected by the impedance change detecting unit.

11. The apparatus according to claim 8 further comprising:
    at least three of the breath sound measuring units disposed adjacent to each other; and
    an impedance change detecting unit detecting changes in impedance between two neighboring electrodes,
    wherein the selecting unit of the breath sound measuring unit selects the plurality of breath sound measuring units as candidate breath sound measuring units based on the changes in impedance between the electrodes, and selects the breath sound measuring unit which exhibits the greatest amplitude of the breath sound synchronous component, among the plurality of the candidate breath sound measuring units.

12. The apparatus according to claim 8 further comprising:
a first pressing member that presses a first breath sound measuring unit among the plurality of breath sound measuring units against the subject;
a second pressing member that presses a second breath sound measuring unit among the plurality of breath sound measuring units against the subject; and
a pressure controlling unit controlling pressure of the first pressing member, when the selecting unit of the breath sound measuring unit selects the first breath sound measuring unit.

13. The apparatus according to claim 12, wherein the first pressing member is an air bag, and the pressure controlling unit controls an amount of air in the air bag.

14. The apparatus according to claim 13 further comprising:
a respiratory signal measuring unit measuring a subject's respiratory signal based on the pressure transmitted to the air bag,
wherein the respiratory condition determining unit further determines the subject's respiratory condition based on the respiratory signal measured by the respiratory signal measuring unit.

15. A computer program product having a non-transitory computer readable medium including programmed instructions for determining respiratory condition, wherein the instructions, when executed by a computer, cause the computer to perform:
measuring a breath sound signal passing through a subject's airway by a breathing;
calculating a first frequency spectrum and a second frequency spectrum by performing frequency conversion, the first frequency spectrum being a frequency spectrum of the breath sound corresponding to a maximum value on an envelope curve, the second frequency spectrum being a frequency spectrum of the breath sound corresponding to a minimum value on the envelope curve, the envelope curve being obtained by performing rectifying integration of the breath sound signal;
extracting a respiratory synchronous component that is difference between the first frequency spectrum and the second frequency spectrum;
detecting a frequency distribution of the respiratory synchronous component; and
determining a subject's respiratory condition worsens when a frequency shift is equal to or greater than a predetermined value, the frequency shift indicating a change between a respiratory synchronous component when the subject is in a normal state and the extracted respiratory synchronous component.

\* \* \* \* \*